(12) United States Patent
Forsythe et al.

(10) Patent No.: US 6,375,999 B1
(45) Date of Patent: *Apr. 23, 2002

(54) METHODS FOR TREATING POTATOES

(76) Inventors: Darol Forsythe, 15401 Cartwright Rd., Boise, ID (US) 83703; John M. Forsythe, 4277 Balivi La., Nampa, ID (US) 83687

( * ) Notice: Subject to any disclaimer, the term of this patent is extended or adjusted under 35 U.S.C. 154(b) by 0 days.

This patent is subject to a terminal disclaimer.

(21) Appl. No.: 09/477,256

(22) Filed: Jan. 4, 2000

Related U.S. Application Data

(63) Continuation-in-part of application No. 08/887,545, filed on Jul. 3, 1997, now Pat. No. 6,010,728, which is a continuation of application No. 08/570,255, filed on Dec. 19, 1995, now abandoned, which is a continuation-in-part of application No. 08/175,620, filed on Dec. 30, 1993, now abandoned, which is a continuation-in-part of application No. 08/133,453, filed on Oct. 7, 1993, now abandoned.

(51) Int. Cl.$^7$ .............................. A23B 7/154; A23B 7/16
(52) U.S. Cl. ..................... 426/310; 426/321; 504/304; 504/357; 514/485; 514/765
(58) Field of Search ................................ 426/302, 309, 426/310, 321, 312, 442, 443; 504/327, 253, 304, 357; 514/485, 765

(56) References Cited

U.S. PATENT DOCUMENTS

| | | | |
|---|---|---|---|
| 3,742,094 A | * 6/1973 | Kishino et al. ............. 260/940 |
| 4,078,480 A | * 3/1978 | Luck ............................ 99/476 |
| 4,226,179 A | * 10/1980 | Sheldon, III et al. ......... 99/475 |
| 4,887,525 A | * 12/1989 | Morgan ........................ 99/476 |
| 5,009,152 A | * 4/1991 | Morgan ........................ 99/476 |
| 5,244,866 A | * 9/1993 | Tayler ......................... 504/253 |
| 5,622,912 A | * 4/1997 | Riggle et al. ................ 504/143 |
| 5,811,372 A | * 9/1998 | Riggle et al. ................ 504/138 |
| 5,918,537 A | * 7/1999 | Forsythe et al. .............. 99/467 |
| 5,965,489 A | * 10/1999 | Forsythe et al. ............. 504/143 |
| 6,010,728 A | * 1/2000 | Forsythe et al. ............. 426/302 |

FOREIGN PATENT DOCUMENTS

WO 95/09535 * 4/1995

* cited by examiner

*Primary Examiner*—Arthur L. Corbin
(74) *Attorney, Agent, or Firm*—TraskBritt

(57) ABSTRACT

A sprout inhibitor for potatoes is introduced into a potato storage facility as a gas phase carried in an air stream. The liquid sprout inhibitor may be heated prior to injection into a flowing air stream or a large surface area of the liquid sprout inhibitor may be exposed to the air stream to induce evaporation of the inhibitor into a gaseous phase. Sprout inhibitors such as dimethylnaphthalene (DMN) and trimethylnaphthalene are especially suitable for introduction to potato storage sheds by thermal fogging or evaporative fogging. A method and composition to promote healing of freshly dug potatoes are further disclosed. Treatment of freshly dug potatoes with DMN either prior to or immediately after storage promotes rapid healing of cuts, abrasions and similar injuries to the potatoes. Stored potatoes first treated with DMN may be later advantageously treated with low levels of CIPC for effective sprout inhibition.

29 Claims, 1 Drawing Sheet

METHODS FOR TREATING POTATOES

RELATED APPLICATION

Figure 1:
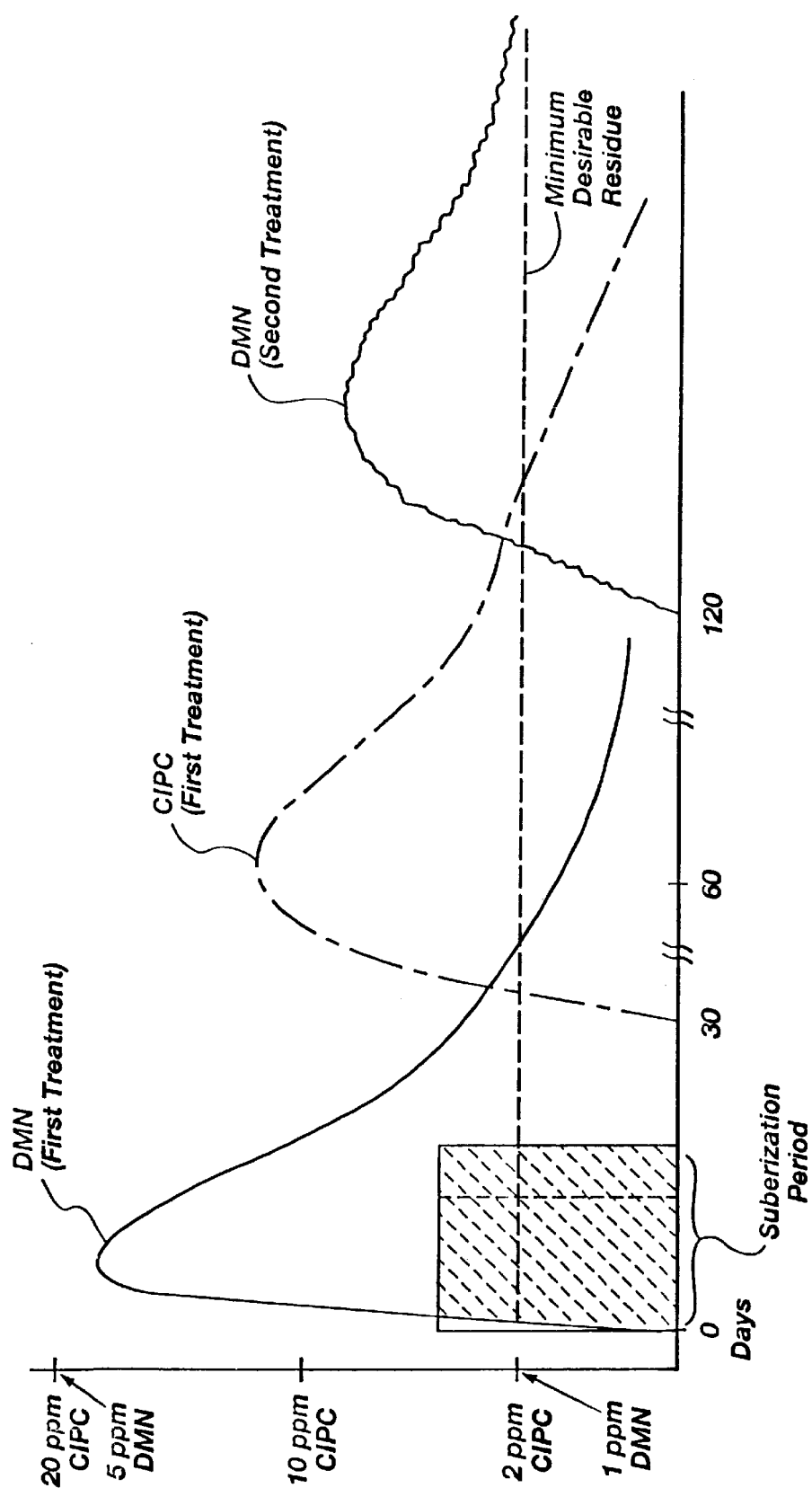

This application is a continuation in-part of application Ser. No. 08/887,545 filed Jul. 3, 1997, now U.S. Pat. No. 6,010,728, which is a continuation-in-part of application Ser. No. 08/570,255 filed Dec. 11, 1995, now abandoned, which is a continuation of Ser. No. 08/175,620 filed Dec. 30, 1993, now abandoned, which is a continuation-in-part of Ser. No. 08/133,453, filed Oct. 7, 1993, now abandoned.

BACKGROUND OF THE INVENTION

1. Field of the Invention

This invention relates to methods and compositions for treating stored potatoes including freshly dug potatoes.

2. State of the Art

A commercial sprout inhibitor has been chemically identified as Chloroisopropyl-N-carbamate (CIPC) which is a solid at room temperature. Various techniques and apparatus have been employed for distributing CIPC throughout a potato storage facility. Generally, CIPC is dissolved in a solvent, e.g., a polar solvent such as methanol, ethylene glycol, etc. and then atomized thermally or by other means and introduced, along with combustion products of the thermal fogging device, into an air stream which is generally the ventilation system for the potato storage facility in order to deposit a certain minor amount of CIPC evenly on all the potatoes in the storage shed.

The technique of distributing CIPC is frequently alluded to as "fogging," especially because the solvent/CIPC solution vapor emanating form a "fogger" forms either minute liquid droplets in the air stream or very fine solid crystals which precipitate from the solution droplets. These droplets or crystals are suspended in air and appear as a fog or cloud. Thus, there is a phase difference between the gas (air) in the ventilating system and the CIPC which is either a liquid or a solid, even though in minute particle form.

It is necessary for CIPC to be in contact with the potato in a storage facility in order for it to be effective. Thus, during a typical storage, usually beginning in about October, one or more treatments of the storage facility with a "dusting" of CIPC via thermal fogging is done.

Prior patents which disclose apparatus and discuss the techniques of distributing CIPCs throughout the potato storage facility are Morgan U.S. Pat. No. 5,009,152, Morgan U.S. Pat. No. 4,887,525, Luck U.S. Pat. No. 4,078,480, and Sheldon U.S. Pat. No. 4,226,179, and Plant U.S. Pat. No. 3,128,170. Sheldon discloses an ultrasound technique for fogging CIPC solutions.

The chemical CIPC has been the principal sprout inhibitor used commercially in agriculture for the past 20 years or more. Other sprout inhibitors have been considered and experimental work has been done with chemicals such as coumarin, fenilin, dimethylnaphthalene (DMN), the latter having three isomers, the 1–4, the 1–6, and the 2–3 and other chemicals. Effectiveness of some of these other potential sprout inhibitors has been reported in the following journals:

Potato Res. 24 (1981) 61–76 Beveridge et al. "The Assessment of Some Volatile Organic Compounds as Sprout Suppressants for Ware and Seed Potatoes."

Potato Res. 24 (1981) 77–88 Beveridge et al. "Dimethylnephthalene as a Sprout Suppressant for Seed and Ware Potatoes."

Potato Res. 27 (1984) 383–392 Filmer et al. "An assessment of 1, 4, 6 -Trimethylnapthalene as a Sprout Suppressant for Stored Potato Tubers."

Photochemistry v. 12 (1973) Mergh et al. "Growth-Inhibitory Volatile Isomatic Compound. Produced by Solanum Tuberosum Tubers."

Although experimental work on such sprout inhibitors as DMN has shown promise, the commercial application of certain isomers DMN and other experimental sprout inhibitors has not been practiced.

In certain small scale experimental efforts, e.g., as described in Beveridge et al., the DMN was introduced into a small closed container by being absorbed on alumina and then allowed to evaporate, apparently to maintain a constant atmosphere of DMN in a closed environment. The alumina powder containing DMN was applied directly to the potatoes.

The potential usefulness of DMN as a potato sprout inhibitor has been disclosed in several publications, as indicated hereinabove.

Similarly, in British Patent Application 9117350, a technique was disclosed for measuring constantly the DMN concentration in the headspace of a potato storage facility. The DMN concentration measuring device interacted with a controller to cause more DMN to be introduced into the headspace when the concentration dropped below a certain minimum value (3 mg/m$^3$) and to cease DMN introduction when it achieved a maximum value of about 6 mg/m$^3$. This technique contemplated continuous introduction of DMN during an entire storage period.

Such a system requires a DMN applicator or injection unit for every storage shed. It also requires an expensive DMN concentration detection device for each storage shed. While such a system might be very appealing to the manufacturer of such an injection/monitor system, it would not be appealing to farmers who would have to buy such a system for each storage shed.

The profitability of storing potatoes for a period of time to await a more favorable potato price is such that it would not financially support the capital expenditure and regular maintenance and attention required of such a sophisticated injection and monitoring system.

The approach taken in B.P. Application 9117350, albeit an expensive one, is a direct application of the law of vapor pressure balancing. If the partial pressure of DMN in a potato storage facility equals the vapor pressure of DMN emanating from a potato, then the escape of DMN from the potato is prevented. Such an approach, straight forward scientifically, ignores a number of critical factors besides capital expenditure, maintenance, etc.

Potato storage facilities are rather large buildings with considerable headspace, voids (space between adjacent potatoes) and are not leak proof. Furthermore, neutralizing DMN respiration would not foreclose respiration of other ingredients from the potatoes. Respiration involves the release of heat. It is therefore necessary to ventilate and cool the potato pile during storage. This is well known and potato storage facilities are equipped with ventilation, duct work and humidifiers. The air inside a potato storage facility is changed very frequently during warm weather; but even during the coldest days of winter in Idaho and Maine, some ventilation may be necessary.

A potato storage facility is not under constant supervision. Most air handling and humidifying systems require infrequent attention. The DMN treatment system proposed in B.P. Application 9117350 would require frequent attention. A constantly operating injector/monitor system is not appropriate for a farm situation. If the monitor malfunctioned, an entire crop of potatoes could be lost. The present method of treating storage facilities with sprout inhibitors is treatment of the facility by skilled applicators with specialized equipment three or four times a year with each treatment, including set up, requiring less than one day.

Potatoes, when being dug are frequently bruised, cut and/or abraded. These injuries to the potatoes oftentimes cause spoilage during shipment, storage and the like. A process known as suberization occurs naturally which tends to heal many of these injuries. However, whenever potatoes are stored, which occurs with a particularly large portion of potatoes harvested in any given year, if healing occurs slowly a significant loss of potatoes can occur through spoilage.

For example, it is relatively common in the potato storage industry to treat potatoes with Chloroisopropyl-N-carbamate (CIPC) to prevent or retard development of sprouts in the potatoes. Even though potatoes are stored at a cool temperature, for example, generally between about 40° and 45° F., sprouting does begin to occur after a couple months of storage. Storage of upwards of six to eight months is typical for a stored potato harvest. Thus, without treatment of a chemical such as CIPC, the stored potatoes become entangled in sprouts and the whole stored lot of potatoes may become economically useless. Although early treatment with CIPC could be advantageous for sprout inhibition purposes, application of CIPC is typically delayed until after suberization has occurred inasmuch as CIPC tends to retard suberization, resulting in accelerated rot and spoilage.

BRIEF SUMMARY OF THE INVENTION

The instant invention involves a method and apparatus for introducing controlled quantities of a liquid sprout inhibitor such as an isomer of dimethylnaphthalene (DMN) into a large potato storage facility in a substantially uniform manner. A liquid sprout inhibitor, for the purposes of this invention, is one which is liquid at room temperature and has a freezing point above about 0° C. and a boiling point below about 300° C.

Liquid sprout inhibitors, unlike solid sprout inhibitors such as CIPC, do not need to be dissolved in a solvent or diluted with some diluent. Although solvents or diluents could be utilized with liquid sprout inhibitors, it is generally preferred that an undiluted liquid sprout inhibitor be introduced as such as a vapor into an air stream which flows throughout the potato storage facility.

It is generally known that some chemicals within a potato begin to diminish at about the same time that sprouting occurs. One of these chemicals is dimethylnaphthalene. Thus, after a certain period of storage under certain conditions, potato chemicals, such as dimethylnaphthalene, begin to migrate through the potato skin, that is, respirate, so that the content of dimethylnaphthalene, for example, remaining in the potato is reduced. It is believed that this reduced quantity of DMN, as well as perhaps some other chemicals, in the potato is a condition that either promotes or permits sprouting.

Thus, the instant invention is directed to a method and means for introducing a certain atmosphere of liquid sprout inhibitor, for example, DMN in the potato storage facility such that the partial pressure of DMN in the atmosphere surrounding the potatoes approaches or, preferably, exceeds the partial pressure of DMN which would be naturally generated by respiring potatoes in the absence of an air stream through the potato storage facility. (Airstreams, especially humidified airstreams, are generally maintained in potato storage facilities to keep the storage temperature preferably between about 40° and 50° F. and at a relatively high humidity, for example, above 80% and preferably above about 90% with a relative humidity of 95% being relatively common. Lower temperatures inhibit sprouting, but also cause starch conversion to sugars, degrading the quality of the potato for certain purposes.)

Several different techniques are desirable for injecting a vapor into the air space surrounding the stored potatoes. One especially effective method is to rapidly heat the liquid sprout inhibitor to evaporate it and to inject it into an airstream at a rate such that the vapor does not condense into droplets. Or, if there is condensation, it is so minimal that any droplets formed are revaporized because of the low content of the liquid sprout inhibitor in the airstream. The heating and/or evaporation of a liquid sprout inhibitor as preferably done in the absence of solvents, dilutents or combustion products.

For example, in treating a potato storage facility with liquid sprout inhibitor such as an isomer of DMN, especially the 1,4 and 1,6 isomers of DMN, it is only necessary to have a very low concentration of DMN in the atmosphere inasmuch as the quantity of DMN in a potato is very low so that only very minor quantities of DMN respire or exit the potato. Thus, only a very low partial pressure for DMN is created in a static air space surrounding a potato by respiration. The purpose of DMN in the atmosphere surrounding potatoes is to stop or reduce the exiting of DMN from the potato. Once DMN exiting starts, it is believed that such departure initiates the process which leads to sprouting. It has been discovered that treatments with DMN on certain types of potatoes which have started to sprout does not reduce significantly the sprouting to any considerable extent unlike treatment with CIPC which generally retard potato sprouting even after sprouting has been initiated. Thus, in applying liquid sprout inhibitors which are found natively in potatoes it is generally preferred to initiate treatment prior to the onset of sprouting and preferably prior to any considerable exiting of DMN, for example, from the stored potato.

In certain of the prior experimental work stored potatoes, for example, were stored in a box with DMN saturated aluminum particles so that DMN was present during the entire time of storage. This is not practical with a large potato storage facility. For one thing, the quantity of DMN utilized would made it prohibitively expensive. Thus, the instant invention is directed to methods and apparatus for actively and economically treating a large potato storage facility with a liquid sprout inhibitor such as a DMN isomer.

A method and composition for treating freshly dug potatoes to promote healing has now been discovered. The method generally involves applying to the potatoes at least small quantities of one or more isomers of dimethylnaphthalene (hereinafter DMN), preferably as promptly after the potatoes are dug as possible, including treatment in the field, treatment during transportation and early treatment in a storage facility. The treatment process may include spraying a concentrated or dilute liquid solution or suspension of DMN onto potatoes immediately after harvesting or during transport or during the early stages of storage to promote the suberization process. Also, once potatoes are placed in a storage facility, the DMN may be applied as a mist or as a vapor. Generally it is desired to have sufficient DMN applied to the potatoes so that at least some DMN is in contact with the injured portion of the potato.

DETAILED DESCRIPTION OF THE INVENTION

The instant invention relates to methods and apparatus for applying a liquid sprout inhibitor to potatoes in a large potato storage facility in an effective and economic manner. Liquid sprout inhibitors for the purposes of this invention are those having a freezing point generally at about 0° C. or lower and a boiling point of at least 100° C. and higher. A particularly effective liquid sprout inhibitor, identified herein also as an "LSI", is selected from the class of dimethylnaphthalene isomers, especially the 1,4 and 1,6 isomers and diphenylamine. Other liquid sprout inhibitors which may be utilized in the instant invention are trimethylnaphthalene isomers, vanillin, coumarin and the like.

The liquid sprout inhibitors of most interest in the instant invention are those which are found naturally in potatoes. These naturally occurring materials are volatile and are generally known to be released, that is respired, from the potato upon a certain elapsed period of time after harvesting. Release of these volatile materials has been associated with the onset of the sprouting process.

A modern larger potato storage facility generally is one which will accommodate 1000 to 10,000 tons of potatoes. These facilities are generally equipped with ventilating systems by which the air flow and humidity within the storage facility is controlled. Frequently, the ventilation system involves a duct work grid beneath the potato stacks so that the full stack of potatoes may be controlled. Such as ventilation system is illustrated in certain patents such as noted hereinabove.

For large potato storage facilities, three principal methods of application are effective. First, a system which introduces the liquid sprout inhibitor (LSI) into the potato storage pile in a substantially uniform manner as a vapor. Frequent periodic applications are made sufficient to retard the loss of volatile agents from the potato and to prevent sprouting. The LSI may be vaporized by a thermal evaporator or by a large surface area evaporation technique exposed to a dynamic air flow. Second, the LSI may be applied in the form of a very fine mist so that minute droplets of LSI become deposited upon the potatoes and may be absorbed or remain upon the potatoes to maintain a high partial pressure of the LSI in the vicinity of the stored potatoes to minimize loss of volatiles and thereby inhibit sprouting. A third method of applying the LSI is to provide it in a solid form, that is wherein the LSI is either reacted with or mixed with another component so that the resulting form is a solid. Blocks of the solid could be placed in the storage shed prior to introduction of the potatoes with the block being designed to gradually evaporate to expose the LSI after a predetermined period of time so that the LSI would then be evaporating during the critical period beginning before sprouting is typically initiated in order to retard and inhibit sprouting. The details of these three methods will be set forth fully hereinafter.

The method of applying LSI to a potato storage shed preferably should be simple and reliable. A technique which permits a storage shed operator to easily and readily check the amount of LSI introduced during a particular period of time is very desirable.

For example, with the addition of vapor LSI to a shed by means of a thermal generator, it is possible by adding a known quantity of LSI to the generator and then operating it for a certain period of time especially under closed circuit conditions, that is, where substantially no air is introduced from outside the shed, then the operator may be secure in the knowledge that such predetermined quantity of LSI has been introduced into the atmosphere surrounding the potatoes. Measuring devices generally are in place on storage sheds to determine temperature of the stored potatoes as well as the relative humidity of the circulating air. For example, it should be possible to add sufficient DMN to the air within a closed shed to raise partial pressure of the DMN to such a level that DMN is absorbed by the potatoes. Thus, the reverse of DMN respiration could be achieved.

It is recognized that a shed may be sealed only for a certain period of time before the storage temperature exceeds the upper storage temperature limit. Also, air within the shed may become too dry or contain too much carbon dioxide. However, if during the period that a shed is sealed, sufficient DMN is introduced as a vapor to elevate the DMN content in the skin of the potato then for a certain period of time there would need to be no further treatments of DMN and the usual cooling and humidifying of the shed could be resumed.

A similar method may be used with respect to an air evaporation system wherein a large surface area of LSI is exposed to an airstream. The evaporation surface generally need to be an extended surface inasmuch as most LSI materials such as DMN have very low vapor pressures at storage temperatures of 35–50° F. Generally storage temperatures are preferably between about 40–45° F. Thus, to have any considerable vaporization, liquid DMN needs to be extended over a large surface. The technique for doing so, however, should be one which is readily directly measurable so that anyone applying the DMN will know from direct observation how much has been applied. For example, a elongated DMN reservoir with a fibrous mat or similar "wicking" material which extends, at least partially, into the airstream may be utilized whereby the LSI is wicked up from its reservoir into a porous fibrous structure through which air may pass and evaporate the LSI adhering to the fibers. If the LSI is too viscous to readily wick into the fibrous material then the reservoir may be heated to reduce the viscosity of the LSI. Also, a small pump may be used to pump an LSI material from its reservoir to a position wherein it may be allowed to cascade over a porous, extended surface to expose a large film area to an air stream.

The technique of the instant invention is to treat a potato storage facility periodically with DMN, or other liquid sprout inhibitor, at a relatively high concentration of LSI within the facility. Concentration of DMN may be maintained at levels significantly higher than 20 $mg/m^3$ and may approach vapor concentrations of 200–500 $mg/m^3$. Such concentrations may be maintained for a short duration, e.g., several days, by significantly reducing the air exchanged within the facility, which may be done for a short duration without adversely affecting the stored potatoes. For example, DMN can be introduced into the facility over a period of a few hours to achieve a high concentration. The facility is then maintained in a sealed condition for several days to a week while the DMN containing air is circulated within the facility. During the coldest months of the winter it is feasible to maintain the facility in a substantially sealed condition for up to a week.

Although, as indicated in the Plant patent, CIPC is not applied until after suberization (wound healing). DMN is preferably applied initially shortly after the potatoes have been put into the facility. Inventor's experience has been that DMN, unlike CIPC, does not retard sprouting once it has begun. Also, unlike CIPC, DMN is not a foreign material to a potato. Thus, absorption of DMN by a potato does not affect the edible nature of the potato.

In a storage facility containing 40,000 bushels (approximately 2,000,000 lbs.) such as described in the example of the Plant patent, approximately 2½ lbs. (approximately 1100 gms.) of DMN would be required per day to maintain a DMN vapor concentration of approximately 12.5 mg/m³ given 10% air exchange at an air rate of about 9.5 cubic feet/minute for the approximate 220,000 cubic feet facility. Assuming a 2% air exchange and a vapor concentration of 125 mg/m³, treatment over a two day period, about ten pounds of DMN would be required. Assuming four treatments per storage season, a total of only about 40 pounds of DMN would be used while practice of the B.P. Application 9117350 technique would require about 500 pounds DMN. Practice according to Beveridge et al. at 100 mg/kg of potatoes (1 part per 10,000 parts) would require a DMN weight approximately 200 lbs. per treatment, or approximately 800 lbs. for a season (four treatments).

During the colder months of the storage season, a facility could be sealed, i.e., no fresh air introduced, treated with a high concentration of DMN as a vapor, e.g., 125 mg/m³ for a period of eight hours, then leave the facility sealed for a period of several days to a week.

Although an early treatment of stored potatoes is generally desirable, a quiescent period of about 30 to about 90 days typically exists in most temperature zones where potatoes are grown and stored before sprouting begins. A treatment with DMN during the latter stages of this quiescent period is required in order for the whole treatment regimen to be successful. Subsequent treatments should be sufficiently frequent to retard DMN respiration sufficiently to prevent the onset of sprouting.

Prior work with DMN appears to have been experimental in nature without addressing the challenges associated with treatment of commercial storage facilities. Commercial storage facilities are often located on remote farms. Storage sheds are large, frequently constructed of sheet metal and are not air tight.

Applying DMN on a carrier to such potatoes within such a facility would generally be impractical. A deep, long pile of potatoes would be difficult to treat with dig material; getting powdered material on potatoes at the bottom of the pile would not be easy. Ventilating of the facility would generally preclude effective filling of the void space with an effective concentration of DMN. At the temperature of storage, 40–50° F., the vapor pressure of DMN is very low and would not create a sufficient concentration of DMN in the storage facility unless ventilation of the facility was ceased for a long period of time, e.g., for many weeks.

However, using the techniques of the instant invention, a high concentration of DMN can be obtained in a relatively short period. Liquid DMN has a boiling point of about 264° C. (~509° F.) but can be readily evaporated by spraying a fine mist of DMN onto a hot surface, e.g., an electrically heated surface having a temperature of about 550 to 650° F.) (~285° C. to ~350° C.). Vapors are then directed through an electrically heated duct into circulating air within a potato storage facility. The facility is sealed, i.e., no outside air is introduced. The introduction of DMN vapor is continued until a predetermined amount of DMN is introduced into the facility. Generally during treatment of a facility, DMN is maintained at a concentration of at least about 12 mg/m³, preferably about 20 mg/m³, and often as high as 30 mg/m³ or even higher.

The approach of the instant invention, unlike the B.P. Application approach, is to "shock" the potato with an substantial quantity of DMN, i.e., treat the facility intensely, to interrupt the normal biological cycle of the potato. Thus, the approach is to cause a potato's biological clock to reset and induce a new quiescent period after each treatment.

The instant invention relates to a method and composition for promoting the healing of freshly dug potatoes. Potatoes during the digging process are often cut, scraped, abraded and injured in various ways. If potatoes are used immediately after being harvested, then these injuries present no problem whatsoever. However, since most potatoes produced commercially are stored for various periods of times, sometimes up to almost a year, the damaged potato tissue is more susceptible to rot, mold, fungi, infestation by insects and like. While potatoes go through a natural "healing" process called suberization wherein the chemical suberin is formed to convert cell tissue into a corky-like protective layer similar to a callous, this suberization process requires some period of time and often some significant spoilage from rot, infection, insect infestation and the like begins prior to the completion of the suberization process. Once these deterioration mechanisms have begun, the likelihood of ultimate spoilage is very great.

Since potatoes which are produced commercially are stored for lengthy periods of time, it is necessary to treat those potatoes to prevent sprout growth during storage which can destroy the economic value of the stored potatoes. Generally, it has been the practice to delay any application of sprout inhibitors such as CIPC until the suberization process has been completed. Application of CIPC, which is currently the most commonly applied sprout inhibitor, is relatively effective as a sprout inhibitor even with delay in application associated with the suberization process. It would be desirable, however, if the application of a sprout inhibitor could be initiated at an earlier stage during the storage process. The suberization process, depending upon the type of potato, humidity, temperature and other conditions, usually requires from several days to several weeks after the potatoes are dug in order for this natural "healing" process to be completed.

The instant invention involves a process and composition whereby freshly dug potatoes may be treated to promote the healing or suberization process. The invention comprises the application of small quantities of one or more of the isomers of dimethyl-naphthalene (DMN) to the potatoes relatively soon after the potatoes are dug. Since dimethyl-naphthalene is a liquid regardless of which isomer is utilized, although the 1,4isomer is generally preferred, a concentrated form of DMN may be applied to the potatoes. The DMN may be applied by immersing the potatoes in a bath of DMN or DMN may be sprayed upon the potatoes or once the potatoes are in a storage facility, the DMN may be applied as a vapor or as a mist. Also, since only very minute quantities of DMN are required in order to promote effectively the potato healing process, DMN may be present in a minor amount in a solution, suspension or an emulsion.

After early treatment with DMN, potatoes so treated may advantageously be treated subsequently with CIPC or other conventional sprout inhibitor.

It is known that DMN is present in potatoes and there have been prior suggestions regarding use of DMN as a sprout inhibitor, for example, in the hereinabove related parent application. Also, certain literature has suggested that the concentration of DMN in the atmosphere surrounding stored potatoes be monitored and when it drops to a certain level that DMN then be added to the atmosphere of the stored facility on a continuous or semi-continuous basis to retain a certain level of DMN in the atmosphere surrounding the potatoes. This latter literature suggestion contemplates a significant delay in treatment with DMN after harvested potatoes have been stored and well after the natural suberization process would have been completed.

The early application of DMN for different purposes than sprout inhibitation has not been heretofore suggested. In the aforementioned parent application, it is suggested that DMN be applied in early stages of storage as a sprout inhibitor. However, as described in other literature, the late treatment of potatoes with DMN would not be effective for the promotion of suberization since the potatoes would have already naturally healed or would have already begun to experience deterioration by way of rot, mold, fungi, insect infestation and the like.

In a preferred embodiment of the instant invention, potatoes are treated with DMN within about forty-eight hours of being harvested. The potatoes at that time may already be in a storage facility and may be treated in the various ways described herein. Effective treatment with DMN at such an early stage promotes rapid healing of the potatoes and thus permits, if desired, earlier applications of a sprout inhibitor. Also, since DMN possesses sprout inhibitation characteristics, the early treatment of potatoes with DMN tends to increase the amount of DMN in the skin and surface layers of the potato and tends to delay sprouting so that such an early application of DMN may accomplish more than the mere healing of injured potatoes.

There are a number of convenient events during the harvesting and storing of potatoes during which DMN may be readily applied. For example, harvested potatoes are generally fed by a conveyor into trucks so that the potatoes may be hauled to storage facilities. The trucks may be equipped with a spray so that as the potatoes are conveyed into the truck, the potatoes may be sprayed on the conveyor or the potatoes may be sprayed as they are entering the truck bed. Also, potatoes are conveyed from the truck to the storage facility and may be sprayed during this conveying process with liquid DMN in either concentrated or dilute form as a solution, suspension or emulsion. Also, it may be convenient that upon filling of a storage facility, which usually is begun within 24 hours of harvest, to seal the storage facility and treat the potatoes with a vapor or mist of DMN. Very large storage facilities may require a week or more to be filled, thus treatment of the potatoes prior to sealing the facility is very desirable.

During this initial storage period, it is typical to cool the stored potatoes since the potatoes begin to respire, which involves heat generation, and are relatively warm from the ground. Long term storage is typically carried out at about 40° to 45° F. Usually it is not difficult to maintain this temperature in potato growing regions such as Idaho, Washington, Oregon, Maine and other large potato growing regions in the United States and throughout the world. These regions tend to be in temperate climates where the storage season occurs during winter and cool outside air may be introduced to maintain a low temperature storage condition. During harvesting, however, the temperatures may not be sufficiently cool and the introduction of a mist of DMN may assist in cooling the air in a potato storage facility to offset some of the heat contained by the freshly dug potatoes and being generated by respiration of the potatoes. Also, it is typical to maintain a relatively high humidity condition for example, about 95% moisture in the air during the storage of potatoes. Thus, the combination of misting water and DMN either as a mixture or jointly evaporated materials may be desirable to promote healing and to control temperature. Generally, healing proceeds better in relatively high humidity conditions.

In experiments conducted with early treatment of potatoes with DMN, it was generally noted that the DMN treated potatoes underwent the suberization process approximately twice as fast as untreated potatoes. The following example demonstrates the effectiveness of the 1,4-isomer of DMN in promoting the healing process of freshly dug potatoes.

A pile of freshly dug potatoes having considerable injuries such as cuts, scrapes and abrasions were sprayed with pure 1,4-dimethyl naphthalene. The pile was located outdoors with a humidity condition of about 40%. Within about two days after spraying, the suberization processes appeared to be complete with only a small portion of the injured potatoes showing any evidence of rot. Although a control sample wasn't used, potatoes with such a large quantity of cuts, abrasions and the like in an exposed, low humidity environment would typically show minimal healing and a considerable amount of rot.

The healing process for injured potatoes appeared to proceed about twice as fast for freshly dug potatoes treated with DMN in comparison to untreated potatoes. Also, the DMN treatment appeared to interrupt the rotting process inasmuch as potatoes showing some signs of spoilage when treated did not show increased rot when inspected periodically over a several week period.

It is not known to what extent DMN and other volatile chemicals found in and near the skin of a potato play a role in the suberization process. Thus, the chemical effect of the instant invention is not fully understood. However, after repeated treatment of injured, freshly dug potatoes, it has been noted that the potatoes healed much more rapidly when treated with DMN than when similarly injured potatoes were not so treated.

Although treatment of injured potatoes with DMN promotes healing in low humidity, high temperature environments, the healing process proceeds most rapidly if the potatoes are exposed during treatment or shortly thereafter to a high humidity, low temperature environment. This is very important for potatoes which are known to undergo a suberization very slowly. The Russet Burbank potato undergoes relatively fast suberization even without DMN treatment and proceeds to heal extremely quickly when subjected to DMN treatment even at low humidity and high temperature conditions.

Thus, for slow healing potatoes it is desirable to treat the potatoes with DMN as quickly as possible after the potatoes are dug and expose them to a high humidity, cool environment as quickly as possible.

As indicated hereinabove, DMN may be applied in a pure form as a liquid spray, as a mist or as a vapor. In diluted form, DMN may be present in a solvent, preferably one which is non-toxic, although even toxic solvents can be used since the treatment is done early and the solvent will completely evaporate by the time stored potatoes are sent to the market.

An aqueous mixture of DMN may also be advantageously applied as a spray, mist or vapor. Water and DMN are immersible, however, vigorous agitation may maintain a substantially evenly distributed suspension of DMN in water. The mixing may be conducted in a tank as in a mixing chamber of a spray or misting machine. Generally, it is preferred that DMN be present with at least 5%, although preferably 10%, by volume of any suspension or solution.

Vaporization of DMN in a substantially sealed environment, e.q., a storage facility or a treatment unit is an effective way of treating potatoes to promote suberization.

Freshly dug potatoes destined for market rather than storage may be treated by spraying or misting in an open environment or by vapors in a sealed environment. Even fresh potatoes which go directly to market may experience considerable spoilage if suberization does not occur promptly. Thus, because DMN is non-toxic, even potatoes destined for immediate sale may be advantageously treated with DMN.

Most potatoes destined for immediate sale are roughly sized, sorted, washed and then boxed or bagged. The sizing is generally conducted automatically by sizing machines. Sorting is often done by hand whereby badly damaged or rotten potatoes are removed from conveyors. Washing is done either in batchwise manner or continuously. The wash water may advantageously contain suspended DMN. The potatoes are then allowed to dry and are later packaged.

EXAMPLE

Potatoes which had been freshly harvested were treated with DMN upon being placed in a storage facility. The potatoes had not completed suberization and contained cuts and bruises. The DMN was applied at a dosage rate which provided an effective initial DMN residue on the potatoes of about 2 to 5 ppm.

It was observed, upon removal of samples of potatoes after suberization had been completed (about 20 days after DMN treatment), that the potatoes had less spoilage than control potatoes which had not received DMN treatment. Also, the suberization process occurred more quickly with the DMN treated potatoes in comparison with untreated controls.

The DMN treated potatoes were later treated with CIPC about 60 days after the DMN treatment. The CIPC was applied at a residue level of about 4 to 10 ppm by thermal fogging.

Later, when the CIPC residue had fallen to an average level of about 2 ppm, a vapor of DMN was introduced to cause a residue level of about 0.5 to about 2 ppm to be deposited on the potatoes.

The graph of FIG. 1 illustrates a desirable protocol for treated stored potatoes.

Initially, e.g. at or near day one in the storage facility or as the potatoes are conveyed into a storage facility, a spray of DMN, preferably 1,4-DMN is applied to provide a residue level of about 2 to 5 ppm. This treatment aids significantly in promoting suberization, healing of cuts, etc., hardness and other desirable characteristics.

Over a period of weeks, the residue level will diminish. Thus, when the residue level reaches an average of about 0.5 to 1.0 ppm of DMN, the potatoes are then fogged with an aerosol of CIPC to place a residue of about 4 to 10 ppm on the potatoes. This treatment may occur typically about 30 to 50 days after the DMN treatment. This CIPC treatment may be effective at lower levels of CIPC residue than would conventionally be applied in the absence of the first DMN treatment.

About 8 to 12 weeks after the CIPC treatment another treatment is done with vapors of DMN (1,4-DMN) for the purpose of maintaining the potatoes in a firm (hard), non-sprouting condition during the remainder of storage and during post-storage shipment and use. A residue of about 2 to 5 ppm is applied.

The second DMN treatment is preferably done when the CIPC residue has dropped to about 2 ppm. This DMN vapor treatment may be conducted with the storage facility sealed for a period of 24 to 48 hours or more. However, this treatment usually occurs some four to five months after storage when outside temperatures are still cool and heat given off by the potatoes will not unduly raise the storage temperature.

It is seen from FIG. 1 that a subsequent treatment with sprout inhibitor occurs before the residue of the previously applied sprout inhibitor falls below the desired minimum, e.g., about 2 ppm for CIPC and about 0.5 ppm for 1,4-DMN.

A further advantage of early treatment with DMN, especially 1,4-DMN, is to minimize the development of silver scruff, a serious potato disease caused by a fungus.

No approved method exists for treating silver scruff. Effective fungicides are not approved for treatment of potatoes. Recently, it has been suggested that silver scruff may be eliminated or minimized if storage is conducted under conditions of low humidity, e.g. 75–85%, rather than 95% plus typically utilized. A disadvantage of low humidity storage is that such potatoes dehydrate and soften. This causes the potatoes to be less acceptable for certain markets and results in some loss of product. It has been discovered, however, that early treatment of such potatoes with 1,4-DMN causes the potatoes to stay hydrated and firm even under storage conditions of 85%, and less, humidity.

Heretofore, treatment of potatoes with DMN has been conducted under desirable storage conditions, that is, humidity of about 95° and temperatures of 42–45° F.

Although various techniques and methods have been described hereinabove, the instant invention is not to be limited thereto, but to be within the scope of the appended claims.

What is claimed is:

1. A method of treating freshly dug potatoes to promote healing comprising:
 applying an isomer of DMN to said freshly dug potatoes.
2. The method of claim 1 wherein said DMN is applied to said potatoes prior to storage.
3. The method of claim 1 wherein said DMN is applied within about two days of being dug.
4. The method of claim 1 wherein said DMN is applied substantially immediately after said potatoes are dug.
5. The method of claim 1 wherein said DMN is applied to said potatoes substantially immediately after storage.
6. The method of claim 5 wherein said DMN is applied as a vapor.
7. The method of claim 5 wherein said DMN is applied as a mist.
8. The method of claim 1 wherein said DMN is applied as a liquid spray.
9. The method of claim 1 wherein said potatoes are in an unwashed condition.
10. The method of claim 1 wherein said DMN is in substantially pure form.
11. The method of claim 1 wherein said DMN is 1,4-DMN.
12. The method of claim 1 wherein said DMN is present with a diluent.
13. The method of claim 12 wherein said DMN is present as at least 5% of the solution.
14. A method of inhibiting the sprouting of tubers comprising:
 applying an alkyl naphthalene to harvested tubers prior to completion of suberization to provide an initial alkyl naphthalene residue sufficient to promote suberization and inhibit sprouting for a prolonged period; and
 applying CIPC to said alkyl naphthalene treated tubers before significant sprouting has occurred, said CIPC applied in a quantity to give an initial CIPC residue greater than the initial alkyl naphthalene residue.
15. The method of claim 14, wherein an alkyl naphthalene is applied to said CIPC treated tubers before significant sprouting has occurred to provide initial residue less than the initial CIPC residue and sufficient to inhibit sprouting for a prolonged period.
16. The method of claim 15, wherein said alkyl naphthalene is 1,4-dimethylnaphthalene.

17. A method of minimizing silver scruff in stored potatoes comprising:
   maintaining the humidity in the vicinity of said potatoes below about 80% relative humidity;
   maintaining the potatoes at a temperature of between about 40 and 48° F.; and
   maintaining a residue of greater than about 0.5 ppm of 1,4-DMN on said potatoes.

18. A method of minimizing dehydration and softening of potatoes stored under conditions of humidities less than about 85% relative humidity comprising:
   treating said potatoes with 1,4-DMN to maintain a residue of at least about 0.5 ppm on said potatoes.

19. A method of applying DMN or an isomer thereof to stored quiescent potatoes in a substantially sealed potato storage facility to maintain said potatoes in a quiescent state comprising:
   applying said DMN, or an isomer thereof as a vapor rapidly in a predetermined amount to achieve a predetermined concentration of at least about 12.5 mg/m$^3$ in the head space of said facility, maintaining said storage facility substantially sealed for a period of time sufficient to cause the DMN or DMN isomer level in the skin of the potatoes to elevate to a level that the quiescent state of the potatoes is maintained, after ventilation is conducted, to control humidity and storage temperature, and ventilating said storage facility with cool humidified air to maintain high humidity and cool temperature within said storage facility.

20. The method of claim 19, wherein said predetermined DMN concentration is above about 50 mg/m$^3$.

21. The method of claim 19, wherein said period of time is at least 24 hours.

22. The method of claim 19, wherein said period of time is at least 36 hours.

23. The method of claim 19, wherein said period of time does not exceed about 72 hours.

24. The method of claim 19, wherein said vapor of DMN is introduced into a circulating air stream within said storage facility.

25. The method of claim 19, wherein said isomer of DMN is 1,4 DMN or 1,6 DMN.

26. The method of claim 19, wherein said method is repeated at least once in said facility during a storage season.

27. The method of claim 19, wherein said vapor concentrate of DMN is at least 125 mg/m$^3$.

28. The method of claim 19, wherein the DMN is applied in less than 24 hours.

29. The method of claim 19, wherein a second application of DMN is made, according to the method of claim 19, to said potatoes while said potatoes are in a quiescent state.

* * * * *

UNITED STATES PATENT AND TRADEMARK OFFICE
CERTIFICATE OF CORRECTION

PATENT NO. : 6,375,999 B1  
DATED : April 23, 2002  
INVENTOR(S) : Darol Forsythe and John M. Forsythe It is certified that error appears in the above-identified patent and that said Letters Patent is hereby corrected as shown below:

Column 1,  
Line 4, after "continuation" delete "in-part"  
Line 31, change "form" to -- from --

Column 5,  
Line 24, after "Such" change "as" to -- a --

Column 6,  
Line 18, change "need" to -- needs --  
Line 56, change the period after "healing)" to a comma Column 7,  
Line 61, after "with" change "an" to -- a --

Column 10,  
Line 58, change "e.q." to -- e.g. --

Column 12,  
Line 18, change "95º" to -- 95% --  
Line 50, change "the" to -- a --

Column 13,  
Line 18, delete the comma after "DMN"

Signed and Sealed this

Eleventh Day of November, 2003

JAMES E. ROGAN  
*Director of the United States Patent and Trademark Office*